(12) United States Patent
Giovanardi et al.

(10) Patent No.: US 12,427,972 B2
(45) Date of Patent: Sep. 30, 2025

(54) METHOD AND APPARATUS FOR MOTION SICKNESS MITIGATION IN A VEHICLE

(71) Applicant: ClearMotion, Inc., Billerica, MA (US)

(72) Inventors: Marco Giovanardi, Melrose, MA (US); Mario Flores Alanis, Cambridge, MA (US); Jack A. Ekchian, Belmont, MA (US); Paul A. DiZio, Bedford, MA (US); James R. Lackner, Lincoln, MA (US); Aditya Chandrashekhar Chetty, Fremont, CA (US); Yu Jiang, Wellesley, MA (US)

(73) Assignee: ClearMotion, Inc., Billerica, MA (US)

( * ) Notice: Subject to any disclaimer, the term of this patent is extended or adjusted under 35 U.S.C. 154(b) by 0 days.

(21) Appl. No.: 17/920,642

(22) PCT Filed: Apr. 26, 2021

(86) PCT No.: PCT/US2021/029182
§ 371 (c)(1),
(2) Date: Oct. 21, 2022

(87) PCT Pub. No.: WO2021/222115
PCT Pub. Date: Nov. 4, 2021

(65) Prior Publication Data
US 2023/0143296 A1 May 11, 2023

Related U.S. Application Data

(60) Provisional application No. 63/015,808, filed on Apr. 27, 2020.

(51) Int. Cl.
*B60W 30/02* (2012.01)
*B60W 10/22* (2006.01)
(Continued)

(52) U.S. Cl.
CPC ......... *B60W 30/025* (2013.01); *B60W 10/22* (2013.01); *B60W 40/08* (2013.01);
(Continued)

(58) Field of Classification Search
CPC .... B60W 30/025; B60W 30/02; B60W 10/22; B60W 10/04; B60W 10/184;
(Continued)

(56) References Cited

U.S. PATENT DOCUMENTS

| 3,937,058 A | 2/1976 | Hilbrands |
| 3,947,004 A | 3/1976 | Taylor |

(Continued)

FOREIGN PATENT DOCUMENTS

| CN | 109791739 A | 5/2019 |
| DE | 10 2015 015 306 A1 | 5/2016 |

(Continued)

OTHER PUBLICATIONS

International Search Report and Written Opinion mailed Aug. 5, 2021 in connection with International Application No. PCT/US2021/029182.

(Continued)

*Primary Examiner* — Hai H Huynh
(74) *Attorney, Agent, or Firm* — Wolf, Greenfield & Sacks, P.C.

(57) ABSTRACT

Various systems and methods are disclosed for predicting, detecting or mitigating motion sickness of one or more occupants of a vehicle. Also, disclosed are systems and methods for measuring aspects of head motion and characteristics of at least one eye an occupant of a vehicle and using that information mitigate motion sickness.

12 Claims, 2 Drawing Sheets

(51) Int. Cl.
*B60W 40/08* (2012.01)
*B60W 50/00* (2006.01)
*G06V 20/59* (2022.01)
*G06V 40/18* (2022.01)

(52) U.S. Cl.
CPC ......... *B60W 50/0097* (2013.01); *G06V 20/59* (2022.01); *G06V 40/18* (2022.01); *B60W 2420/403* (2013.01); *B60W 2540/221* (2020.02); *B60W 2540/225* (2020.02)

(58) Field of Classification Search
CPC ...... B60W 10/20; B60W 10/30; B60W 40/08; B60W 40/10; B60W 50/0097; B60W 2420/403; B60W 2540/225; B60W 2540/221; B60W 2040/0872; G06V 20/59; G06V 40/18; B60R 16/037; B60G 2400/90; B60G 2800/91; A61B 5/1128; A61B 5/163; A61B 5/18
USPC .......................................... 701/36, 37, 41, 70
See application file for complete search history.

(56) References Cited

U.S. PATENT DOCUMENTS

| | | | |
|---|---|---|---|
| 8,892,304 B2 | 11/2014 | Lu et al. | |
| 9,868,332 B2 * | 1/2018 | Anderson | A61B 5/4023 |
| 9,994,228 B2 * | 6/2018 | Krueger | A61B 5/02055 |
| 10,300,760 B1 | 5/2019 | Aikin et al. | |
| 10,926,773 B2 * | 2/2021 | Vulcu | B60N 2/0273 |
| 11,541,797 B2 * | 1/2023 | Dhaens | B60G 17/06 |
| 11,738,773 B2 * | 8/2023 | Yeom | B60W 40/08 |
| | | | 701/26 |

| | | |
|---|---|---|
| 2008/0275606 A1 | 11/2008 | Tarasinski et al. |
| 2014/0152792 A1 | 6/2014 | Krueger |
| 2015/0120149 A1 | 4/2015 | Worrel et al. |
| 2017/0120932 A1 | 5/2017 | Szczerba et al. |
| 2017/0129335 A1 | 5/2017 | Lu et al. |
| 2017/0136842 A1 | 5/2017 | Anderson et al. |
| 2018/0178808 A1 | 6/2018 | Zhao et al. |
| 2019/0133511 A1 | 5/2019 | Migneco et al. |
| 2019/0191127 A1 | 6/2019 | Koravadi |
| 2019/0269321 A1 | 9/2019 | Murakami et al. |

FOREIGN PATENT DOCUMENTS

| | | |
|---|---|---|
| DE | 102004022581 B4 | 8/2017 |
| EP | 0 162 818 A1 | 11/1985 |
| EP | 0 963 867 A1 | 12/1999 |
| EP | 2 233 332 A2 | 9/2010 |
| EP | 2 431 218 A1 | 3/2012 |
| EP | 3303025 A1 | 4/2018 |
| JP | 2004-299570 A | 10/2004 |
| JP | 2005-326962 A | 11/2005 |
| JP | 2007-236644 A | 9/2007 |
| JP | 2008-120271 A | 5/2008 |
| JP | 2008-265692 A | 11/2008 |
| JP | 6591085 B2 | 10/2019 |

OTHER PUBLICATIONS

Karlsson et al., Motion Sickness—Physiological and psychological influences on motion sickness. Jan. 1, 2012. pp. 1-90, XP055543941. Retrieved on Jan. 17, 2019 from the Internet: http://publications.lib.chalmers.se/records/fulltext/162898.pdf.

* cited by examiner

METHOD AND APPARATUS FOR MOTION SICKNESS MITIGATION IN A VEHICLE

RELATED APPLICATIONS

This application is a national stage filing under 35 U.S.C. § 371 of International Patent Application Serial No. PCT/US2021/029182, filed Apr. 26, 2021, which claims the benefit of priority under 35 U.S.C. § 119(e) of U.S. Provisional Application Ser. No. 63/015,808, filed Apr. 27, 2020, the contents of each of which are incorporated herein by reference in their entirety.

FIELD

Disclosed embodiments are related to mitigating motion sickness in a vehicle.

BACKGROUND

It is commonly believed by researchers that motion sickness is a consequence of sensory conflict. Sensory conflict may occur when two divergent signals are received by the central nervous system from various biosensors (for example, the vestibular system, the sense of sight, or proprioception).

SUMMARY

In some embodiments, a method of mitigating an aspect of motion sickness experienced by an occupant of a vehicle, includes: (i) monitoring at least one saccadic parameter, of at least one eye of a vehicle occupant, as the occupant performs a visual task, while being transported in the motor vehicle; (ii) determining whether a value of the saccadic parameter has exceeded a preset threshold value, or is outside a preset range of values; and (iii) based at least partly on the determination in (ii), modifying an operation of at least one subsystem of the vehicle. The subsystem may be, for example, a propulsion system, a steering system, a braking system, a navigation system, an HVAC system, an interior or ambient lighting system, an entertainment or music system, and/or a suspension system. As used herein, the term "saccadic parameter" refers to a parameter that defines, or is related to, ocular function or behavior and which exhibits a value, or changes in value, that may be indicative or predictive of the onset or severity of motion sickness. At least one saccadic parameter used in this method may be: a fixation rate, a forward saccade ratio, a saccade amplitude, a backward saccade amplitude, a backward saccade ratio, an eye velocity, an average pupil diameter change, an average positive pupil diameter velocity, an average negative pupil diameter velocity, an average pupil diameter velocity, a number of pupil dilation events, a number of pupil constriction events, an average or peak reading speed, and an average fixation length. Additionally or alternatively, this method may include, based at least partly on the value of the at least one saccadic parameter, determining: (a) a level of motion sickness that the occupant will or is likely to experience (b) that the occupant has an increased likelihood of experiencing motion sickness and/or (c) that, after a time delay, a particular level of motion sickness will or is likely to be experienced by the vehicle occupant. In this method, the suspension system may be for example: a chassis or whole vehicle suspension system, suspension system of at least one seat, and/or a suspension system of a platform such as a desk, bed, or work station in the vehicle. This method may include the use of one or more cameras to monitor eye motion, such as for example, saccadic motions of the eye. Such a camera or cameras may be located in any appropriate location for monitoring eye motion of a vehicle occupant during the performance of a visual task. Such cameras may be, for example, one or more cameras secured to: a laptop computer, a computer monitor, a cell phone, a tablet, a display of a computing device, and/or a point on the interior of the passenger compartment. This method may also include determining a value of at least one parameter related to or that characterizes the head motion of an occupant that is performing a visual task, wherein determining the level of motion sickness the occupant will likely experience and/or the time delay after which a particular level of motion sickness may be experienced is also based on the value of the parameter related to or characterizing the head motion. In this method, determining a value of at least one parameter related to or that characterizes head motion may include measuring head displacement, velocity, acceleration, and/or jerk of the head in roll, pitch, yaw, lateral, longitudinal, and/or heave. As used herein, the term "aspect of motion sickness" refers to the severity level of motion sickness or one or more symptoms associated with motion sickness.

In some embodiments, a method of mitigating an aspect of motion sickness experienced by an occupant of a vehicle, includes: (i) monitoring an aspect of head motion of the occupant as the occupant is transported in the motor vehicle; (ii) determining a value of at least one parameter that is related to the aspect of head motion; (iii) determining that the occupant is will, or is likely to experience motion sickness, or has a likelihood of experiencing motion sickness based at least partly on the value determined in (ii); and based at least partly on the determination in (ii), modifying an operation of at least one subsystem of the vehicle, the subsystem which may be: a propulsion system, a steering system, a braking system, a navigation system, an HVAC system, an internal lighting system, an entertainment system and/or a suspension system. Additionally or alternatively, this method may include, based at least partly on the value of the at least one parameter related to the aspect of head motion, determining: (a) a level of motion sickness that the occupant will or is likely to experience (b) that the occupant has an increased likelihood of experiencing motion sickness or (c) that, after a time delay, a particular level of motion sickness will or is likely to be experienced by the vehicle occupant. In this method the suspension system may be for example: a chassis or whole vehicle suspension system, suspension system of at least one seat, and/or a suspension system of a platform such as a desk or work station. Additionally, this method may include the use of a camera to monitor head and/or eye motion, such as for example, saccadic motions of the eye. Such a camera may be located in any appropriate location where it is able to monitor eye motion of a vehicle occupant during the performance of a visual task. Such cameras may be, for example, one or more cameras secured to: a laptop computer, a computer monitor, a cell phone, a tablet, a display of a computing device, and the vehicle itself. The method may also include determining a value of at least a second parameter that is related to a motion of an eye of the occupant, wherein the determining in step (ii) is also at least partly based on the value of the second parameter. In this method the second parameter may be based on: a fixation rate, a forward saccade ratio, a saccade amplitude, a backward saccade amplitude, a backward saccade ratio, an eye velocity, an average pupil diameter change, an average positive pupil diameter velocity, an average negative pupil diameter velocity, an average pupil diameter velocity, a number of pupil dilation events, a number of pupil constriction events, or an average fixation length. As used herein, the term "aspect of head motion" refers to one or more characteristics of head motion, e.g., a magnitude, frequency, or type (e.g., heave, pitch, and/or roll) of the motion of a person's head.

Some embodiments may include a vehicle with a passenger compartment; a camera located in the passenger compartment, the camera being configured and arranged to monitor a saccadic parameter while the vehicle is moving and the occupant is performing a visual task; at least one processor configured and arranged to receive information about the motion of the eye and to determine a value of a first parameter related to the motion of the eye; and a second processor configured and arranged to determine a likelihood that the occupant will experience motion sickness based at least partially on the value of the first parameter. In some embodiments the visual task may include reading task or watching a video. In some embodiments first processor and the second processor may be the same processor.

In some embodiments a vehicle with a passenger compartment may include a first camera and/or other optical sensor located in the passenger compartment that is configured and arranged to monitor a vehicle occupant's eye, while the vehicle is moving and the occupant is performing the visual task. Also included in the passenger compartment may be a second camera and/or other sensor that is configured and arranged to monitor an aspect of a motion of the head (for example the pitch, roll, and/or heave) of the vehicle occupant while the vehicle is moving and the occupant is performing the visual task. The embodiment may also include a first processor configured and arranged to receive information from, e.g., the first camera and based on that information determine that there is an increased likelihood of motion sickness. The embodiment may also include a second processor configured and arranged to receive information from the second camera and/or other sensor and, based on that information, to control the motion of at least a portion of the vehicle, thereby reducing the likelihood of motion sickness by altering the aspect of the motion of the head of the vehicle occupant. In some embodiments the visual task may involve reading or watching a video. In some embodiments the first processor and the second processor may be the same processor.

In some embodiments, a method of mitigating an aspect of motion sickness experienced by an occupant of a vehicle may include monitoring an aspect of head motion of the occupant (such as for example head pitch, roll, or heave) as the occupant is transported in the motor vehicle and determining that the occupant has an increased likelihood of experiencing motion sickness after a time delay. The method may also include modifying the operation of a vehicle subsystem to alter the aspect of the head motion, and, after a period of modified operation, determining that the likelihood of motion sickness has diminished to a sufficient degree and returning the operation of the vehicle subsystem to its pre-modified state.

In some embodiments, a method of operating a vehicle to transport an occupant in the vehicle may include monitoring a state parameter of an eye of the occupant, as the occupant is transported while performing a visual task; and modifying the operation of a vehicle subsystem at least partially based on the monitoring in step (a). In some embodiments the monitored state parameter may be, for example: a fixation rate of the eye of the occupant, a forward saccade ratio of the eye of the occupant, a saccade amplitude of the eye of the occupant, a backward saccade amplitude of the eye of the occupant, a backward saccade ratio of the eye of the occupant, an eye velocity of the eye of the occupant, an average pupil diameter change of the eye of the occupant, an average positive pupil diameter velocity of the eye of the occupant, an average negative pupil diameter velocity of the eye of the occupant, an average pupil diameter velocity of the eye of the occupant, a number of pupil dilation events of the eye of the occupant during a predetermined period, a number of pupil constriction events of the eye of the occupant during a predetermined period, an average or peak reading speed of the eye of the occupant, and/or an average fixation length of the eye of the occupant. In some embodiments, the vehicle subsystem may be, for example, an active suspension system, a semi-active suspension system, a propulsion system, and a steering system.

As used herein, the term "state parameter of an eye" refers to a characteristic of the eye or a motion of the eye (e.g., a magnitude of the motion, a frequency of the motion, a fixation rate, a forward saccade ratio, a saccade amplitude, a backward saccade amplitude, a backward saccade ratio, an eye velocity, an average pupil diameter change, an average positive pupil diameter velocity, an average negative pupil diameter velocity, an average pupil diameter velocity, a number of pupil dilation events, a number of pupil constriction events, an average or peak reading speed, and an average fixation length).

The contents of U.S. Pat. No. 9,868,332 entitled "Methods and systems for controlling vehicle body motion and occupant experience," filed Jun. 3, 2016 are incorporated herein by reference in their entirety. This patent discloses controlling one or more subsystems of a vehicle to mitigate various motions, in one or more frequency ranges, in order to mitigate motion sickness.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various nonlimiting embodiments when considered in conjunction with the accompanying figures. In cases where the present specification and a document incorporated by reference include conflicting and/or inconsistent disclosure, the present specification shall control.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings.

DETAILED DESCRIPTION

Figure 1:
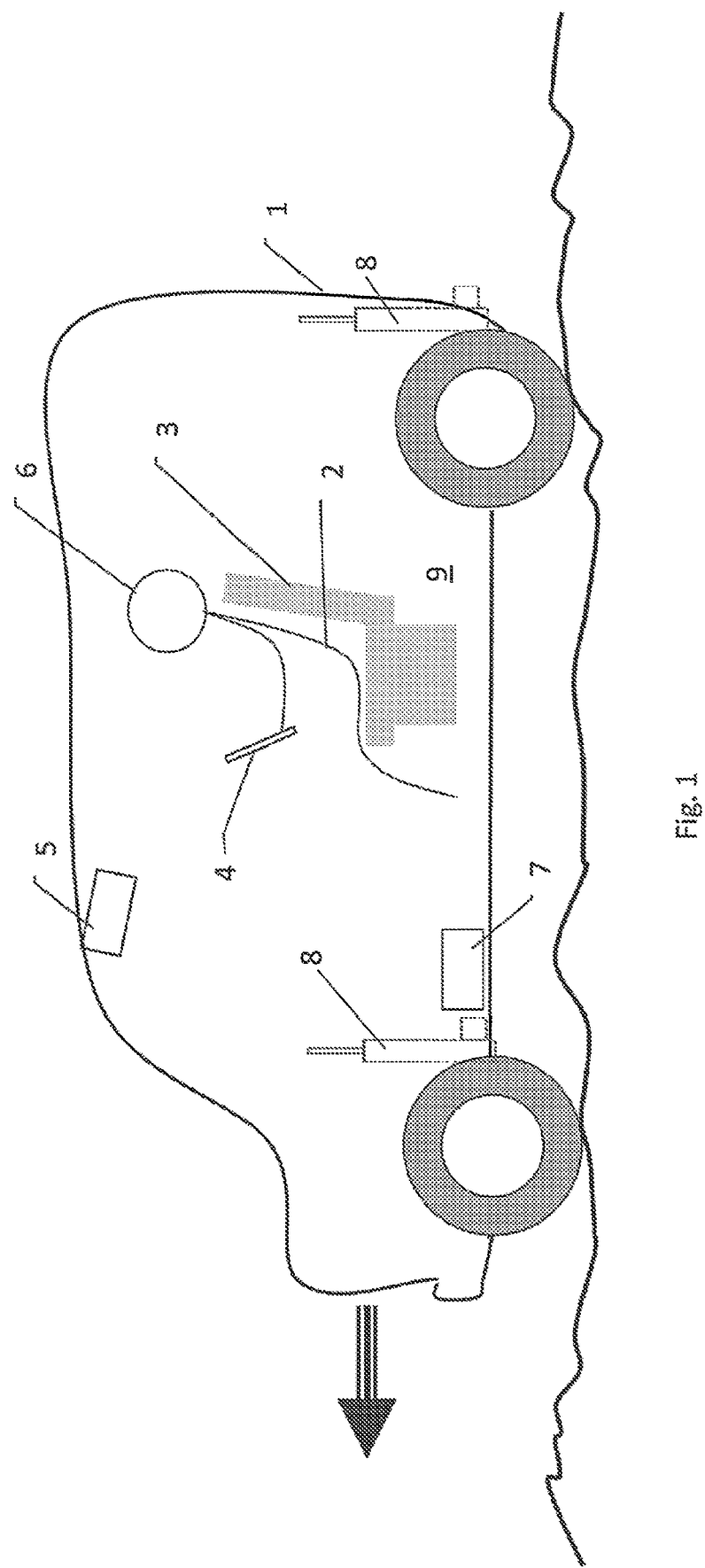
FIG. 1 illustrates a vehicle occupant performing a task, that involves the use of vision, in a vehicle.

Various systems and methods are disclosed for predicting the onset of and/or for avoiding or mitigating motion sickness in a vehicle.

Inventors have recognized that the performance of visual tasks or tasks that may involve vision, such as for example reading from a book or electronic monitor, watching a video, playing video games, repairing a mechanism, etc. while being transported in a vehicle, such as a bus, van or car, etc. may cause motion sickness, augment its severity, extend its duration, and/or accelerate its onset. Inventors have also recognized that the performance of tasks, that have a visual component, while in a moving vehicle may cause motion sickness and/or adversely affect the acuity of the person performing the task. Inventors have also recognized the magnitude, frequency and/or type (i.e., heave, roll, pitch) of head motion (e.g., experienced in the absolute reference frame, and/or in the frame of the reference of the vehicle and/or the passenger compartment) while performing a visual task may determine, e.g., the severity, duration and/or timing of motion sickness. Inventors have also recognized that head motion in one or more frequency ranges, and/or in one or more degrees of freedom may trigger mechanisms to suppress a person's vestibular ocular reflex (VOR) and that the amount of energy expended in the suppression of VOR may affect the onset, duration, and/or severity of motion sickness. Additionally, the inventors have recognized that normal saccadic eye movements, present in non-accelerating environments, during the performance of visual tasks, such as for example reading, may be disturbed in an environment that is accelerating. Inventors have also recognized that, in an accelerating environment, changes in certain parameters that describe saccadic movements or eye movements in general, i.e., saccadic parameters, may be used as predictors of the onset or severity of motion sickness. It is noted that, even in a vehicle traveling, for example, at a constant forward speed, a vehicle occupant (and the occupants head) may be exposed to accelerations in the absolute reference frame. These accelerations, which may be for example, heave, roll or pitch accelerations, may result from, for example, road induced disturbances that may be caused by interactions between the vehicle and the road surface.

Saccadic parameters may include for example one or more of: fixation rate, forward saccade ratio, saccade amplitude, backward saccade amplitude, backward saccade ratio, eye velocity, average pupil diameter change, average positive pupil diameter velocity, average negative pupil diameter velocity, average pupil diameter velocity, number of pupil dilation events, number of pupil constriction events, or average fixation length. Saccadic parameters may include other quantities that characterize eye movement saccades, and the disclosure is not so limited.

Inventors have also recognized that acceleration of the head of an occupant, in a moving vehicle, may be used as both a predictor of the onset and or severity of motion sickness as well a control parameter in its mitigation. Applicants have recognized that determining the severity and duration of head motion in one or more frequency ranges may be used as a predictor. However, one or more parameters that describe or are related to head motion may be used as control parameters during mitigation of motion sickness.

Inventors have also recognized that acceleration of the head of an occupant, in a moving vehicle may trigger that person's vestibular ocular reflex (VOR). The normal function of VOR is to maintain the eyes in the proper orientation so the image of a visual target, such as words on a page or screen or a snippet of a video frame, remain stable on the retina. This is accomplished by involuntary movements of the eyes in the head that are effectively equal and opposite to head movements. In the absence of such compensatory eye movements, the visual image would dart about, especially during nonvoluntary movements of the head. Without VOR, visual orientation would normally be difficult if not impossible to maintain. However, the inventors have recognized that in a moving vehicle, where vehicle occupants and the visual target may be jostled about, for example due to road-induced disturbances, VOR may be counterproductive. In a moving vehicle, because both the visual target and an occupant's head may move, eye motion caused by VOR may result in the image of the visual target slipping with respect to the retina. Inventors have recognized that in order to prevent this behavior, VOR may be involuntarily suppressed by some vehicle occupants. Applicants have also recognized that this suppression, if it persists over a long enough period, may induce motion sickness, fatigue and/or other undesirable effects.

Inventors have also recognized that certain saccadic parameters may be used as indicators or predictors of the onset of motion sickness. Therefore, changes in the value of one or more saccadic parameters may be determined by using one or more cameras and/or other optical sensors as eye trackers and an associated processor. An example of commercially available eye tracking systems, that may be used to detect changes in saccadic parameters, are the Tobii Pro Fusion and the Tobii Pro Nano manufactured by Tobii AB, in Danderyd, Sweden. These devices have two integrated cameras and may be attached to, for example, the monitor of a laptop computer.

In some embodiments an eye tracking sensor may be used to measure changes in one or more saccadic parameters. A microprocessor may then be used to determine if the magnitude of the change in one or more saccadic parameters is greater than a threshold value. For example, inventors have recognized that an increase in the percentage backward saccades is greater than 30% it may indicate that there is an increased likelihood of the onset of motion sickness. It is noted that other saccadic parameters and/or changes in the values of one or more saccadic parameters may be use as predictors of the onset and/or severity of motion sickness and the disclosure is not so limited.

In some embodiments, cameras and/or sensors, such as head-mounted IMUs or accelerometers, may be used to monitor head motion such as head pitch, roll and/or heave in one or more frequency ranges. Once it is determined that the likelihood of motion sickness has exceeded a threshold amount, various vehicle subsystems, such as for example, a vehicular or seat active suspension system may be used to mitigate head motion in one or more frequency ranges. Head motion measurements may be used as a feedback parameter in such a control arrangement.

In FIG. 1, a vehicle 1 travelling along a road contains an occupant 2 sitting on a seat 3 and performing a visual ocular task on device 4, along with a camera or other optical sensor 5 that monitors motions of the head 6 of the occupant and/or one or more parameters associated with eye motion. A control unit 7, which may include one or more microprocessors, is located in the vehicle and processes the sensor information. The microprocessor-based control unit 7 may control and/or mitigate the occupants head and/or eye motion by controlling active or semi-active vehicle suspension actuators 8 and/or seat suspension system actuator 9.

Figure 2:
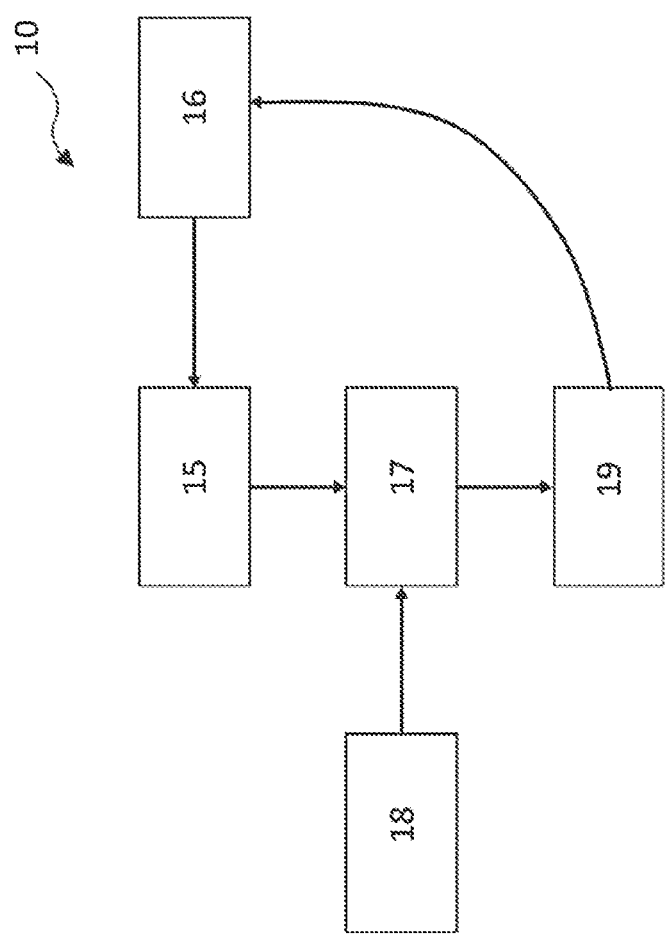
FIG. 2 illustrates a block diagram of a control system for mitigating motion sickness by controlling the head and/or eye motion of a vehicle occupant.

FIG. 2 illustrates a control flow process 10 of an embodiment. Motion 16 of the occupant's head and/or of the eyes are picked up by the sensor 15 (e.g., camera) and supplied to the processing unit 17. In some embodiments, information from other sources 18 may be added to this process and used to create a control output to control system 19. Control system 19 may include for example a set of actuators to move the vehicle and/or seat, and/or it may include actuation of other systems as described here to modify the state of motion sickness of the occupant. This in turn may lead to a change in eye and/or head motion 16.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

Embodiments have been described where the techniques are implemented in circuitry and/or computer-executable instructions. It should be appreciated that some embodiments may be in the form of a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Various aspects of the embodiments described above may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "having," "containing," "involving," and variations thereof herein, is meant to encompass the items listed thereafter and equivalents thereof as well as additional items.

Having thus described several aspects of at least one embodiment, it is to be appreciated that various alterations, modifications, and improvements will readily occur to those skilled in the art. Such alterations, modifications, and improvements are intended to be part of this disclosure, and are intended to be within the spirit and scope of the principles described herein. Accordingly, the foregoing description and drawings are by way of example only.

The invention claimed is:

1. A method of mitigating an aspect of motion sickness experienced by an occupant of a vehicle, the method comprising:
   (a) monitoring at least one saccadic parameter related to at least one eye of the occupant as the occupant performs a visual task while being transported in the vehicle;
   (b) determining that a magnitude of a change in a value of the at least one saccadic parameter has exceeded a preset threshold value; and
   (c) based at least partly on the determination in (b), modifying an operation of at least one subsystem of the vehicle, the at least one subsystem being selected from the group consisting of: a propulsion system, a steering system, a braking system, a navigation system, an HVAC system, and a suspension system.

2. The method of claim 1, wherein the at least one saccadic parameter is selected from the group consisting of: a fixation rate, a forward saccade ratio, a saccade amplitude, a backward saccade amplitude, a backward saccade ratio, an eye velocity, an average pupil diameter change, an average positive pupil diameter velocity, an average negative pupil diameter velocity, an average pupil diameter velocity, a number of pupil dilation events, a number of pupil constriction events, and an average fixation length.

3. The method of claim 1, further comprising, based at least partly on the value of the at least one saccadic parameter, determining a level of motion sickness the occupant is likely to experience or a time delay after which a particular level of motion sickness is likely to be experienced by the occupant.

4. The method of claim 3, further comprising determining a value of at least a parameter related to a head motion of the occupant, wherein determining the level of motion sickness the occupant is likely to experience or the time delay after which a particular level of motion sickness is likely to be experienced is also based on the value of the parameter related to the head motion.

5. The method of claim 4, wherein the head motion of the occupant is selected from the group consisting of head pitch, head roll, and head heave.

6. The method of claim 1, wherein the at least one subsystem of the vehicle is the suspension system and the suspension system is selected from the group consisting of a chassis suspension system, a seat suspension system, and a platform suspension system.

7. The method of claim 1, wherein the monitoring in step (a) includes use of a camera selected from the group consisting of a camera secured to: a laptop computer, a computer monitor, a cell phone, a tablet, and the vehicle.

8. A vehicle comprising:
   a passenger compartment;
   a camera located in the passenger compartment, the camera being configured and arranged to monitor a motion of an eye of a vehicle occupant while the vehicle is moving and the vehicle occupant is performing a visual task;
   a first processor configured and arranged to receive information about the motion of the eye and to determine a value of a saccadic parameter related to the motion of the eye; and
   a second processor configured and arranged to determine a likelihood that the vehicle occupant will experience motion sickness based at least partially on a change in a magnitude of the value of the saccadic parameter.

9. The vehicle of claim 8, wherein the visual task involves reading.

10. The vehicle of claim 8, wherein the first processor and the second processor are the same processor.

11. The vehicle of claim 8, wherein the change in magnitude of the saccadic parameter is compared to a threshold value.

12. The vehicle of claim 8, wherein the saccadic parameter is a backward saccade.

* * * * *